US009184048B2

(12) United States Patent
Takahashi et al.

(10) Patent No.: US 9,184,048 B2
(45) Date of Patent: Nov. 10, 2015

(54) METHOD OF MANUFACTURING CELLULAR ELECTROPHYSIOLOGY SENSOR CHIP (71) Applicant: Panasonic Corporation, Osaka (JP)

(72) Inventors: Makoto Takahashi, Osaka (JP); Masaya Nakatani, Hyogo (JP); Hiroshi Ushio, Osaka (JP); Takeki Yamamoto, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 529 days.

(21) Appl. No.: 13/713,065

(22) Filed: Dec. 13, 2012

(65) Prior Publication Data

US 2013/0102099 A1 Apr. 25, 2013

Related U.S. Application Data (62) Division of application No. 12/677,977, filed as application No. PCT/JP2009/003423 on Jul. 22, 2009, now abandoned.

(30) Foreign Application Priority Data

Aug. 4, 2008 (JP) .................................. 2008-200775

(51) Int. Cl.
*H01L 21/02* (2006.01)
*G01N 33/487* (2006.01)

(52) U.S. Cl.
CPC .... *H01L 21/02356* (2013.01); *G01N 33/48728* (2013.01)

(58) Field of Classification Search
CPC .................. G01N 33/48728; H01L 21/02365
See application file for complete search history.

(56) References Cited

U.S. PATENT DOCUMENTS 6,936,462 B1 8/2005 Owen et al.
2003/0113833 A1 6/2003 Oka et al.
(Continued)

FOREIGN PATENT DOCUMENTS

JP 2007-202420 A 8/2007
JP 2008-187968 A 8/2008
(Continued)

OTHER PUBLICATIONS

Supplementary Partial European Search Report for EP 09804680.8 dated Nov. 28, 2012.
(Continued)

*Primary Examiner* — J. Christopher Ball
*Assistant Examiner* — Maris R Kessel
(74) *Attorney, Agent, or Firm* — RatnerPrestia (57) ABSTRACT A cellular electrophysiology sensor is adapted to measure an electrical change of a test cell. A chip for the sensor includes a diaphragm, and a thermally-oxidized film mainly containing silicon dioxide on the diaphragm. The diaphragm includes a silicon layer and a silicon dioxide layer on an upper surface of the silicon layer. A through-hole passing through the silicon layer and the silicon dioxide layer is formed. The through-hole has an opening which opens at the silicon dioxide layer and is adapted to capture the test cell. The thermally-oxidized film is provided on an inner wall surface of the through-hole, and unified with the silicon dioxide layer at the opening of the through-hole. This cellular electrophysiology sensor chip can stably capture the test cell and provides a gigaseal stably even if test cells have different properties.

4 Claims, 8 Drawing Sheets

(56) References Cited

U.S. PATENT DOCUMENTS

| | | | |
|---|---|---|---|
| 2004/0005696 A1 | 1/2004 | Vestergaard et al. | |
| 2005/0212095 A1 | 9/2005 | Vestergaard et al. | |
| 2005/0221282 A1 | 10/2005 | Owen et al. | |
| 2006/0003145 A1* | 1/2006 | Hansen et al. | 428/131 |
| 2009/0152110 A1 | 6/2009 | Hiraoka et al. | |

FOREIGN PATENT DOCUMENTS

| | | |
|---|---|---|
| JP | 2009-19958 A | 1/2009 |
| JP | 2009-72130 A | 4/2009 |
| JP | 2009-198180 A | 9/2009 |
| WO | WO 99/66329 A1 | 12/1999 |
| WO | WO 02/055653 A1 | 7/2002 |
| WO | WO 03/089564 A1 | 10/2003 |
| WO | WO 2004/015741 A2 | 2/2004 |
| WO | WO 2005/078083 A1 | 8/2005 |
| WO | 2007/055043 | 5/2007 |
| WO | WO 2007/138902 A1 | 7/2009 |

OTHER PUBLICATIONS

Curtis, et al., "Seal Formation in Silicon Planar Patch-Clamp Microstructures", Journal of Microelectromechanical Systems, pp. 974-983, vol. 17, No. 4, Aug. 2008, US.

Naoya Yasuhara et al, 2P1-3F-G3, Injection of Conducting Material into Insulating Micro Nozzle Structures for Biomedical Electrode Needles, ROBOMEC'03, 2003 JSME Conference on Robotics and Mechatronics, May 23, 2003, Japan.

International Search Report (Japanese language), Jul. 22, 2009.

Storm et al., Fabrication of solid-state nanopores with single-nanometre precision, Nat Mater., vol. (8), pp. 537-540 (2003).

Summons to attend oral proceedings dated Feb. 6, 2015 for the related European Patent Application No. 09804680.8.

Curtis J C et al: "Seal Formation in Silicon Planar Patch-Clamp Microstructures", Journal of Microelectromechanical Systems, IEEE Service Center, US, vol. 17, No. 4, Aug. 1, 2008, pp. 974-983.

Gyeong S. Hwang: "On the origin of the notching effect during etching in uniform high density plasmas", Journal of Vacuum Sciences and Technology B, vol. 15, No. 1, Jan. 1, 1997, pp. 70-87.

* cited by examiner

METHOD OF MANUFACTURING CELLULAR ELECTROPHYSIOLOGY SENSOR CHIP

This application is a divisional of U.S. patent application Ser. No. 12/677,977, filed Mar. 12, 2010, which is a U.S. National Phase Application of PCT International Application PCT/JP2009/003423, filed Jul. 22, 2009, the entire disclosures of which are incorporated herein by reference.

TECHNICAL FIELD

The present invention relates to a cellular electrophysiology sensor chip used to measure electrophysiology activities of cells, to a cellular electrophysiology sensor using the cellular electrophysiology sensor chip, and to a method of manufacturing the cellular electrophysiology sensor chip.

BACKGROUND ART

Substrate-type probes formed by a microfabrication technique have recently attracted attentions for electrophysiologically measuring an ion channel in a cell membrane. These probes do not require a skilled operation to insert a micropipette to each cell unlike conventional patch clamp methods, thus being suitable for an automated system having a high throughput.

Figure 10:
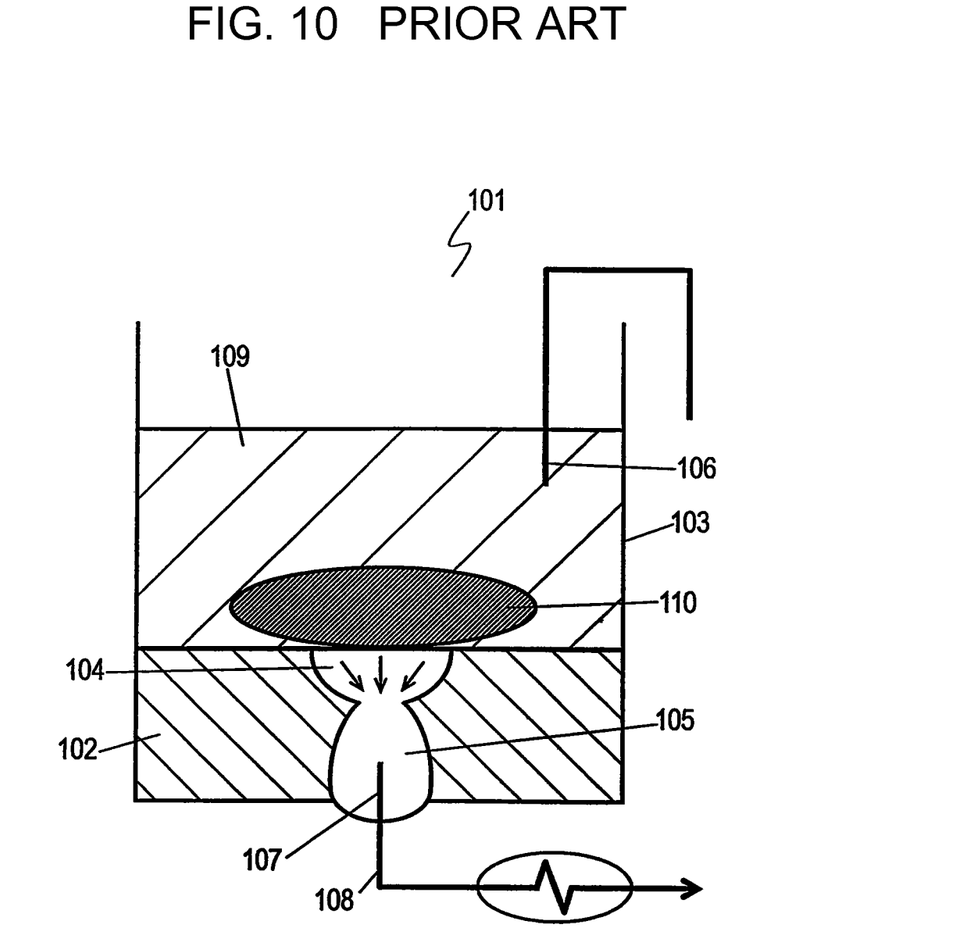
FIG. 10 is a cross-sectional view of a conventional cellular electrophysiology sensor.

FIG. 10 is a cross-sectional view of conventional cellular electrophysiology sensor 101 disclosed in Patent Document 1. Cellular electrophysiology sensor 101, a substrate-type probe, includes substrate 102 and electrode bath 103 located above substrate 102. Substrate 102 has through-hole 105 penetrating from an upper surface of substrate 102 to a lower surface of substrate 102.

First electrode 106 is provided in electrode bath 103. Second electrode 107 is provided in through-hole 105. Second electrode 107 is connected to a signal detector via wiring 108.

An operation of cellular electrophysiology sensor 101 will be described below.

First, electrolyte solution 109 and test cell 110 are injected into electrode bath 103. Test cell 110 is captured and held at opening 104 of through-hole 105.

Test cell 110 is sucked with a suction pump from a lower side of through-hole 105 and is retained while attached securely to opening 104. Specifically, through-hole 105 functions as a tip end hole of a micropipette. Thus, while test cell 110 is attached securely to opening 104, a change in a voltage between first electrode 106 and second electrode 107 before and after a reaction is measured, or a change in a current before and after the reaction is measured. Then, a potential difference between outside and inside of the cell is calculated to analyze a function of an ion channel of test cell 110 and a physiological property, such as a pharmacological reaction, of the cell having an electrophysiology property cell.

In conventional cellular electrophysiology sensor 101, test cell 110 captured by through-hole 105 may not be securely attached onto opening 104. When test cell 110 is not attached securely onto opening 104, the cell does not provide a high electrical resistance (a gigaseal) between first electrode 106 and second electrode 107 reproducibly and stably.

Individual test cells 110 have different properties, such as surface property and elasticity. These individual differences influence the gigaseal. Through-hole 105 is very small, and hence, a dust attached to through-hole 105 deteriorates the gigaseal around through-hole 105. This prevents through-hole 105 from sucking and capturing test cell 110 securely and stably, thus deteriorating the gigaseal.

Patent Document 1: WO02/055653

SUMMARY OF THE INVENTION

A cellular electrophysiology sensor is adapted to measure an electrical change of a test cell. A chip for the sensor includes a diaphragm, and a thermally-oxidized film mainly containing silicon dioxide on the diaphragm. The diaphragm includes a silicon layer and a silicon dioxide layer on an upper surface of the silicon layer. A through-hole passing through the silicon layer and the silicon dioxide layer is formed. The through-hole has an opening which opens at the silicon dioxide layer and is adapted to capture the test cell. The thermally-oxidized film is provided on an inner wall surface of the through-hole, and unified with the silicon dioxide layer at the opening of the through-hole.

This cellular electrophysiology sensor chip can stably capture the test cell and provides a gigaseal stably even if test cells have different properties.

DETAILED DESCRIPTION OF PREFERRED EMBODIMENT

Figure 1:
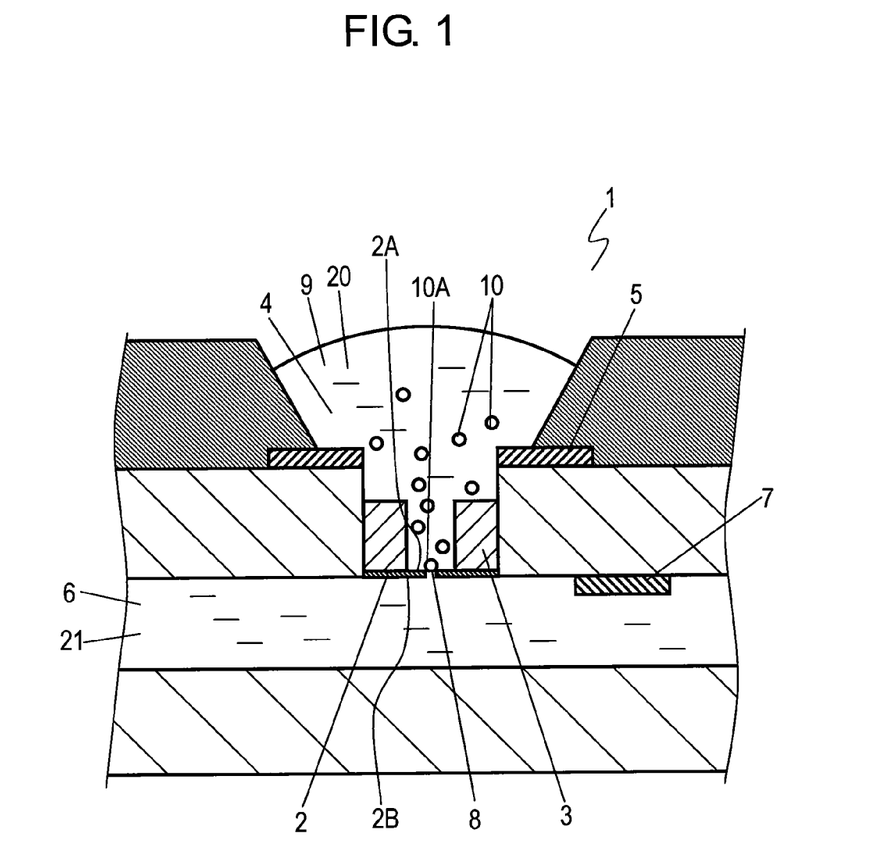
FIG. 1 is a cross-sectional view of a cellular electrophysiology sensor according to an exemplary embodiment of the present invention.

FIG. 1 is a cross-sectional view of cellular electrophysiology sensor 1 according to an exemplary embodiment of the present invention. Cellular electrophysiology sensor 1 includes chip 3 including diaphragm 2, electrode bath 4 provided on upper surface 2A of diaphragm 2, electrode bath 6 provided on lower surface 2B of diaphragm 2, electrode 5 provided in electrode bath 4, and electrode 7 provided in electrode bath 6. Electrode baths 4 and 6 are configured to be filled with electrolyte solutions 20 and 21, respectively. Electrode 5 is electrically connected to electrolyte solution 20 filling electrode bath 4. Electrode 7 is electrically connected to electrolyte solution 21 filling electrode bath 6. Electrodes 5 and 7 detect a potential difference between electrode baths 4 and 6. Diaphragm 2 has through-hole 8 penetrating from upper surface 2A to lower surface 2B. Electrode baths 4 and 6 communicate with each other through through-hole 8.

Electrode bath 4 is configured to be filled with electrolyte solution 20 and culture solution 9 having cells 10 dispersed therein. Culture solution 9 itself can be electrolyte solution. Culture solution 9 is sucked through through-hole 8 and cell 10A out of cells 10 blocks through-hole 8. Then, cell 10A drastically increases an electrical resistance between electrolyte solutions 20 and 21 in electrode baths 4 and 6, thereby providing a gigaseal. Cell 10A out of cells 10 is a test cell which can be measured in physiochemical phenomenon.

Figure 2:
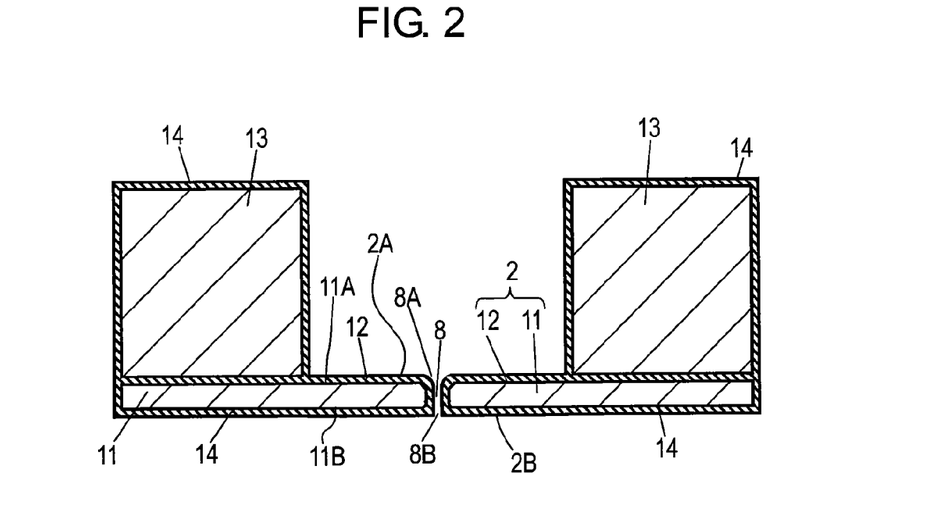
FIG. 2 is a cross-sectional view of the cellular electrophysiology sensor chip according to the embodiment.

The configuration of chip 3, an important component, of cellular electrophysiology sensor 1 will be described below. FIG. 2 is a cross-sectional view of chip 3. An SOI substrate including two silicon layers and a silicon dioxide layer sandwiched between the silicon layers is finely processed by a photo etching to simultaneously provide a lot of chips 3 precisely. Chip 3 includes diaphragm 2 having through-hole 8 therein and silicon layer 13 joined to diaphragm 2.

Diaphragm 2 includes silicon layer 11, and silicon dioxide layer 12 provided on upper surface 11A of silicon layer 11. Silicon dioxide layer 12 is so hydrophilic that air bubbles are suppressed and easily removed, accordingly allowing the potential difference to be measured accurately. Air bubbles remaining near through-hole 8 during the measurement of the potential difference decrease an electrical resistance between electrode solutions 20 and 21 in electrode baths 4 and 6 and deteriorate a gigaseal drastically, accordingly preventing an accurate measurement. Silicon dioxide layer 12 preferably has a thickness ranging from 0.3 to 10 μm.

Diaphragm 2 may have a small thickness of a few micrometers. In order to be easily handled and mounted in manufacturing processes, silicon layer 13 is provided at an outer periphery of diaphragm 2. Specifically, silicon layer 13 functions as a supporter for retaining chip 3 to maintain the mechanical strength of the chip, and stores liquid, such as electrolyte solution 20 and culture solution 9. Thus, silicon layer 13 is not an essential component for chip 3, and has a predetermined size determined appropriately depending on the shape and structure of chip 3.

Diaphragm 2 including silicon layer 11 and silicon dioxide layer 12 has at least one through-hole 8 penetrating the diaphragm from upper surface 2A to lower surface 2B. Diaphragm 2 may have through-holes 8 penetrating the diaphragm from upper surface 2A to lower surface 2B. This structure allows test cells 10A to be measured simultaneously with a high S/N ratio.

A surface of chip 3 has thermally-oxidized film 14 that is formed by heating surfaces of silicon layers 11 and 13. Thermally-oxidized film 14 is made of silicon dioxide and covers the surface of diaphragm 2. Thermally-oxidized film 14 also covers the surfaces of silicon layers 11 and 13 constituting chip 3 together with silicon dioxide layer 12 to secure insulation and to increase hydrophilicity. Thermally-oxidized film 14 preferably has a thickness ranging from 100 to 2000 nm. Thermally-oxidized film 14 having a thickness smaller than 100 nm does not completely cover the surfaces of silicon layers 11 and 13. Thermally-oxidized film 14 having a thickness exceeding 2000 nm requires a long time to form thermally-oxidized film 14, hence reducing productivity of chip 3.

Thermally-oxidized film 14 is provided on Inner wall surface 8C of through-hole 8 to cover silicon layer 11. This structure easily captures cell 10A and improves the gigaseal. Thermally-oxidized film 14 on inner wall surface 8C of through-hole 8 can be formed by thermally-oxidizing silicon layers 11 and 13 of chip 3 in a heat-treatment furnace. This process allows thermally-oxidized film 14 entirely covering exposed surfaces of silicon layers 11 and 13 can be formed efficiently. This structure improves the hydrophilicity of chip 3 to improve the wettability with liquid, thus suppressing the surface of chip 3 from having air bubbles produced thereon.

The silicon dioxide, an insulating material, covering the surface of diaphragm 2 enhances electrical insulation between electrodes 5 and 7, hence allowing the electrophysiological phenomenon of cell 10A to be measured accurately and reproducibly.

Figure 3A:
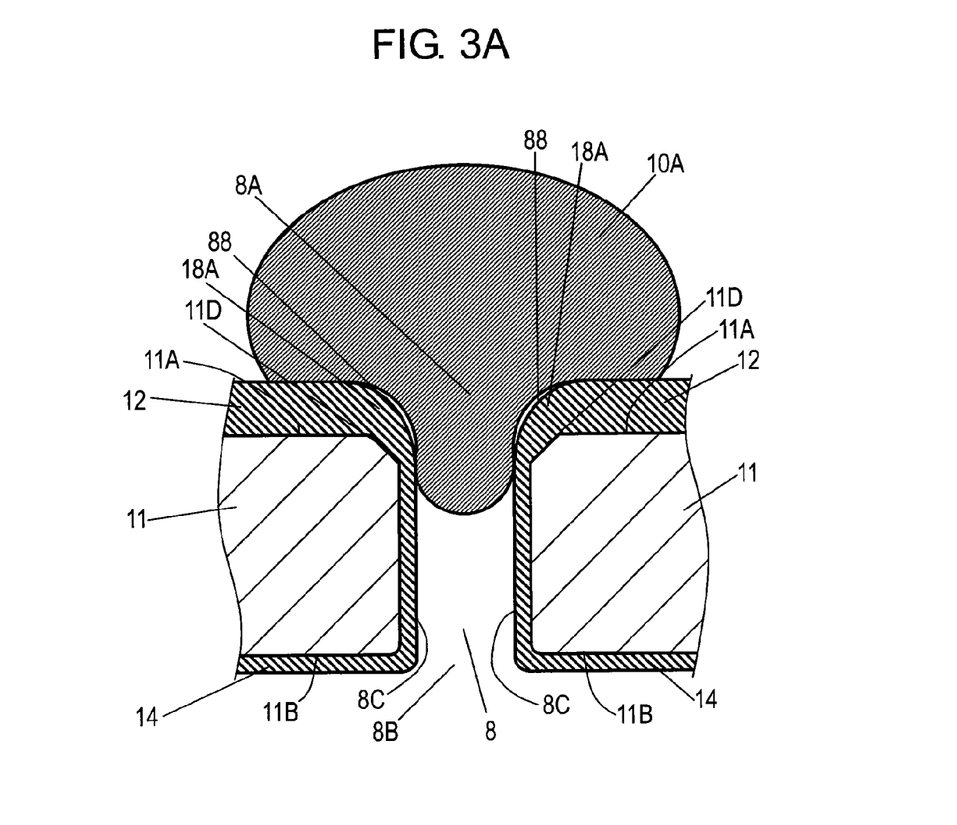
FIG. 3A is a schematic enlarged cross-sectional view of the cellular electrophysiology sensor chip according to the embodiment.

FIG. 3A is a schematic enlarged cross-sectional view of chip 3 adapted to capture test cell 10A. Through-hole 8 has opening 8A opening in silicon dioxide layer 12 and opening 8B opening at a side opposite to opening 8A. Opening 8A is adapted to capture test cell 10A. As shown in FIG. 3A, thermally-oxidized film 14 and silicon dioxide layer 12 are to opening 8A connected via a smooth surface while continuously forming a curved surface along inner wall surface 8C of through-hole 8.

Figure 3B:
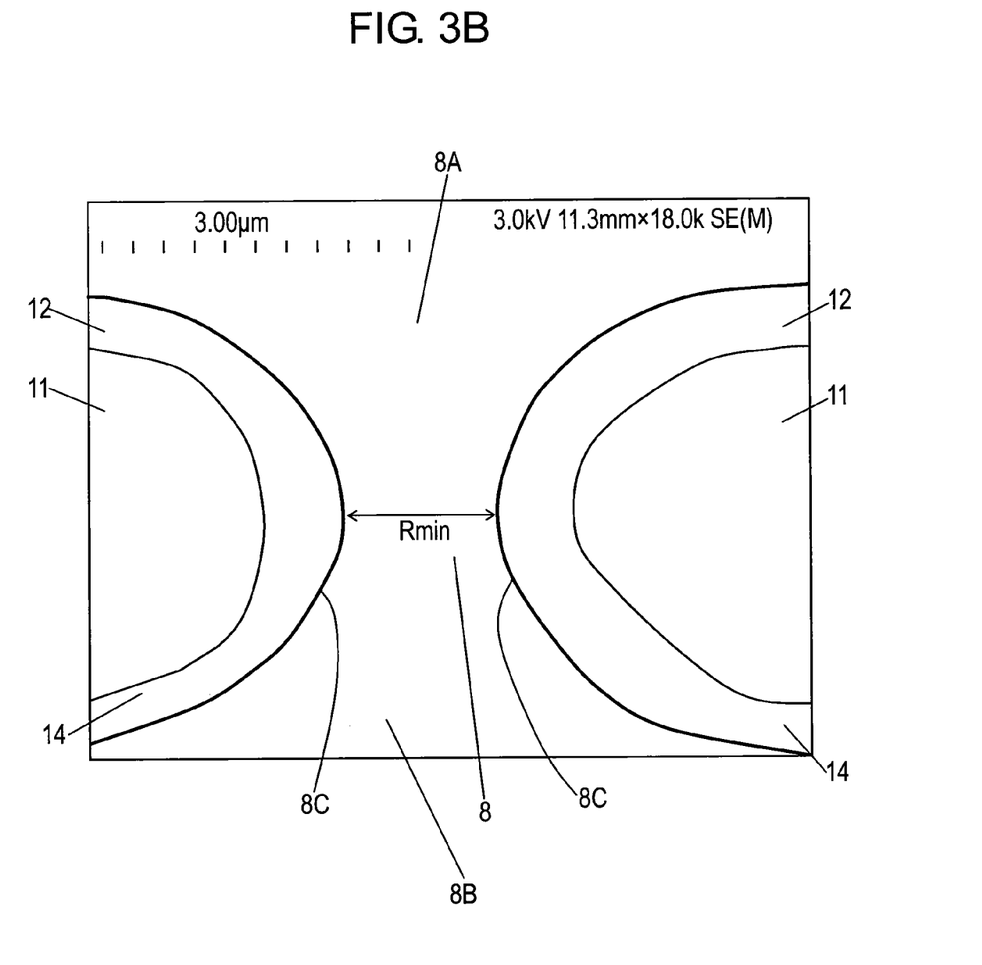
FIG. 3B is an enlarged cross-sectional view of the cellular electrophysiology sensor chip according to the embodiment.

FIG. 3B is an enlarged cross-sectional view of actual chip 3. As shown in FIG. 3B, inner wall surface 8C of through-hole 8 is preferably a smooth curved surface protruding toward an inside of through-hole 8 so as to have minimum inner diameter Rmin between openings 8A and 8B. As shown in FIG. 3B, through-hole 8 preferably has minimum inner diameter Rmin substantially at the middle between openings 8A and 8B and has a diameter increase to flare to opening 8A. Silicon dioxide layer 12 preferably has a thickness not smaller than 0.3 μm. Silicon dioxide layer 12 having a thickness not smaller than 0.3 μm can form a smooth melting surface and can form a smooth curved surface.

Surface 88 of thermally-oxidized film 14 at opening 8A of through-hole 8 is also a melting surface mainly containing silicon dioxide. Surface 88 is formed by forming thermally-oxidized film 14 to subsequently melt silicon dioxide layer 12 and thermally-oxidized film 14 while maintaining a temperature not lower than 1150° C. in, e.g. a thermal treatment furnace, to make surface 88 smooth.

Opening 8A and inner wall surface 8C of through-hole 8 preferably have root-mean-square roughness Rq not larger than 5.0 nm. Root-mean-square roughness Rq is defined as a square root of an average value of the squares of deviations of measured values of the surface roughness from an average value of the distribution of the measured values of the surface roughness.

According to this embodiment, through-hole 8 has minimum inner diameter Rmin of 3 μm. Minimum inner diameter Rmin is preferably determined appropriately depending on the size, shape, and property of cell 10. When test cell 10A has a size ranging from about 5 to 50 μm, for example, through-hole 8 preferably has minimum inner diameter Rmin not larger than 3 μm to accept test cell 10A attached to the opening. Through-hole 8 has a depth not larger than 15 μm.

Next, a method of measuring a cell potential with cellular electrophysiology sensor 1 will be described below with reference to FIGS. 1 to 3A.

First, as shown in FIG. 1, liquid in culture solution 9 is replaced to fill electrode bath 4 with electrolyte solution 20 (extracellular liquid) containing cells 10 including test cell 10A suspended therein. Electrode bath 6 is filled with electrolyte solution 21 (intracellular fluid). Through-hole 8 functions as a boundary between electrolyte solution 20 and electrolyte solution 21.

According to this embodiment, cells 10 are muscle cells of mammal. Electrolyte solution 20 contains about 155 mM of $K^+$ ions, about 12 mM of $Na^+$ ions, about 4.2 mM of $Cl^-$ ions. Electrolyte solution 21 contains about 4 mM of $K^+$ ions, about 145 mM of $Na^+$ ions, and about 123 mM of $Cl^-$ ions. Electrolyte solutions 20 and 21 can have the same composition.

Next, cells 10 and electrolyte solution 20 are sucked into through-hole 8 by pressurizing the solutions from the upper surface of diaphragm 2 or depressurizing the solutions from the lower surface. This operation allows test cell 10A out of cells 10 to be captured and retained on opening 8A so as to block through-hole 8.

Next, a fine hole is formed in test cell 10A by sucking the solutions from the lower surface of diaphragm 2 or by putting medicinal agent, such as nystatin, from beneath diaphragm 2.

Then, stimulation is given to test cell 10A from above diaphragm 2. This stimulation can be chemical stimulation, such as chemical agent or toxic substance, or physical stimulation, such as a mechanical displacement, light, head, electricity, or an electromagnetic wave.

Upon actively reacting to this stimulation, test cell 10A discharges or absorbs ions via a channel in the cell membrane. This activity changes potential gradients at the inner side and the outer side of the cell, hence allowing electrodes 5 and 7 shown in FIG. 1 to detect such an electrical change to examine the cell in, e.g. pharmacological reaction.

Next, a method of manufacturing cellular electrophysiology sensor 1 according to this embodiment will be described below. FIGS. 4 to 7 are cross-sectional views of chip 3 of cellular electrophysiology sensor 1 for illustrating a method of manufacturing chip 3.

Figure 4:
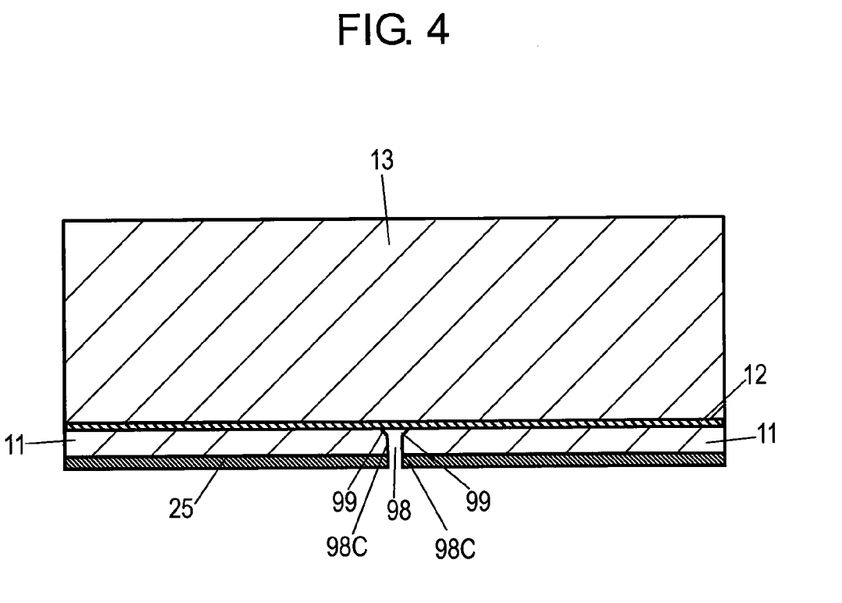
FIG. 4 is a cross-sectional view of the cellular electrophysiology sensor chip for illustrating a method of manufacturing the sensor chip according to the embodiment.

First, a wafer including silicon layer 11, silicon dioxide layer 12 on silicon layer 11, and silicon layer 13 on silicon dioxide layer 12 is prepared. Silicon dioxide layer 12 is positioned between silicon layers 11 and 13. This wafer is commercially-available as an SOI substrate. According to this embodiment, silicon layer 11 has a thickness of 15 μm, silicon dioxide layer 12 has a thickness of 1 μm, and silicon layer 13 has a thickness of 250 μm.

As shown in FIG. 4, resist mask 25 is formed on a surface of silicon layer 11. Resist mask 25 is patterned to have a mask hole having a shape substantially identical to a predetermined shape of the cross section of through-hole 8.

Next, silicon layer 11 is etched to form through-hole 98 reaching silicon dioxide layer 12. This etching is executed preferably in dry etching that can provide accurate microfabrication. During the dry etching, etching gas facilitating the etching and suppression gas suppressing the etching are alternately used so as to form through-hole 98 having a high aspect ratio, the ratio of the inner diameter of the through-hole to the depth of the hole According to this embodiment, the etching gas is $SF_6$ and the suppression gas is $C_4F_8$. Plasma is produced by an inductive coupling of an external coil. The etching gas of $SF_6$ is introduced into the plasma, and generates F radical. Then, the F radical reacts with silicon layer 11 to chemically etch silicon layer 11.

Then, a high-frequency voltage is applied to silicon layer 11 so as to generate a negative bias voltage on silicon layer 11. Then, positive ions ($SF_5^+$) contained in the etching gas collide vertically with silicon layer 11. The ions bombardment physically etches silicon layer 11. Thus, the dry etching proceeds in a direction vertically to silicon layer 11 (downward).

When the suppression gas, $C_4F_8$, is used on the other hand, no high-frequency voltage is applied to silicon layer 11, thereby generating no bias voltage on silicon layer 11. This operation prevents $CF^+$ contained in the suppression gas, $C_4F_8$, from deflecting, and thus, allowing $CF^+$ to be attached uniformly onto the inner wall surface of hole 98 of silicon layer 11 to form an even film.

$CF^+$ deposits to function as a protection film suppressing the etching. This protection film is formed not only on a wall surface of through-hole 98 but also on a bottom of the through-hole. However, the protection film formed on the bottom can be more easily removed by the bombardment by positive ions ($SF5^+$) than the protection film formed on the inner wall of the through-hole, thereby causing the etching to proceed downward. The etching proceeds to allow through-hole 98 to reach a surface of silicon dioxide layer 12. Since silicon dioxide layer 12 is not etched under the above etching conditions, the etching for forming through-hole 98 in the depth direction stops at silicon dioxide layer 12. Further etching causes etching ions to be accumulated on an exposed surface of silicon dioxide layer 12. If the etching further proceeds, ions of the etching gas repel the ions of the etching gas accumulated on the surface of silicon dioxide layer 12, accordingly causing the etching ions to start shifting in a lateral direction. Thus, near silicon dioxide layer 12, recess 99 is formed in inner wall surface 98C of through-hole 98 in silicon layer 11 near silicon dioxide layer 12, along a lower surface of silicon dioxide layer 12. Recess 99 has a flaring shape having a diameter gradually increasing from silicon layer 11 to silicon dioxide layer 12. Silicon layer 11, a conductive material, and silicon dioxide layer 12, an insulating material, are layered at recess 99. The ions of the etching gas tend to be accumulated on silicon dioxide layer 12, the insulating material, more easily than on silicon layer 11, the conductive material. Therefore, the accumulated ions of the etching gas repel entering ions of the etching gas to cause the etching to proceed in the lateral direction, thereby forming recess 99. Recess 99 has a depth of about 1 μm. The depth of recess 99 can be controlled by the period of time of the etching.

The etching gas can be $CF_4$ and the suppression gas can be $CHF_3$.

Next, silicon dioxide layer 12 is etched by dry etching to form through-hole 97 connected to through-hole 98. Plasma-excited Ar gas flows straight to function as etching gas, and the mixture gas of $CF_4$ and Ar contains a large amount of etching agent, such as argon ions, that performs spattering. The mixture gas of $CF_4$ and Ar flows straight from an opening of through-hole 98 to etch only silicon dioxide layer 12, insulating material.

Although the mixture gas slightly etches silicon layer 11, the conductive material, the protection film formed during the forming of through-hole 98 can substantially maintain the shapes of through-hole 98 and recess 99.

As described above, since two materials constituting the layered structure of diaphragm 2 have different etching rates to the same gas, silicon layer 11 made of conductive material is etched while silicon dioxide layer 12 made of insulating material is not etched. Further, silicon dioxide layer 12 made of insulating material is etched while silicon layer 11 made of conductive material is not etched. This operation provides through-hole 98 easily with a predetermined shape.

Figure 5:
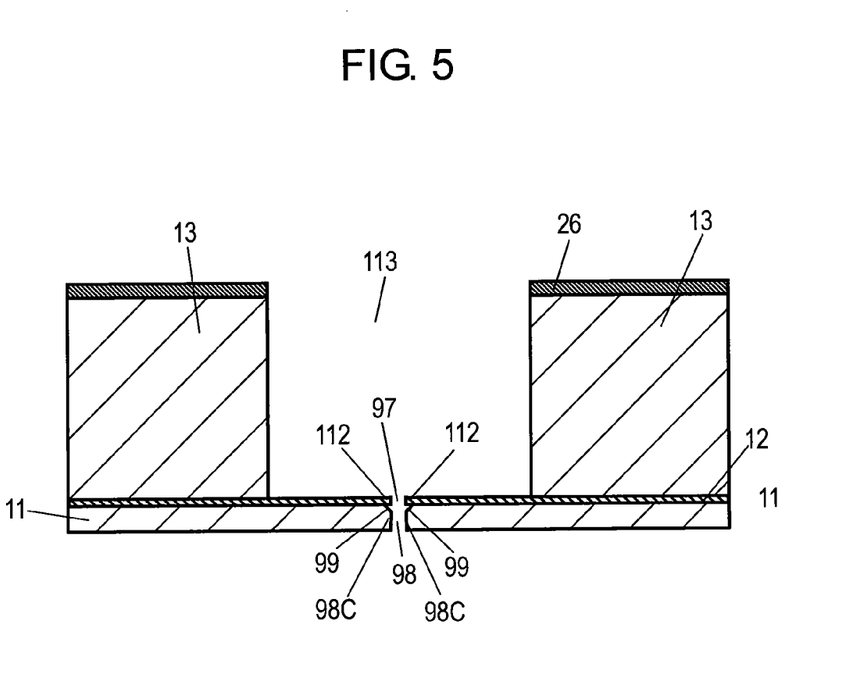
FIG. 5 is a cross-sectional view of the cellular electrophysiology sensor chip for illustrating the method of manufacturing the sensor chip according to the embodiment.

Next, as shown in FIG. 5, resist mask 26 is formed on an upper surface of silicon layer 13, and then silicon layer 13 is etched under the same etching conditions as those of silicon layer 11 to form recess 113. This etching in the depth direction stops at silicon dioxide layer 12. Silicon dioxide layer 12 functions as an etching stop layer for stopping the etching. Portion 112 of silicon dioxide layer 12 protrudes at opening 99 of through-hole 98.

Then, the wafer is placed in a heat-treatment furnace in air and is heated in an atmosphere containing oxygen so as to oxidize the surfaces of silicon layers 11 and 13 to form thermally-oxidized film 14 evenly on the surfaces of silicon layers 11 and 13. Thermally-oxidized film 14 has a thickness ranging from 200 to 230 nm. Thermally-oxidized film 14 can be formed at a temperature not lower than of 700° C.

Figure 6:
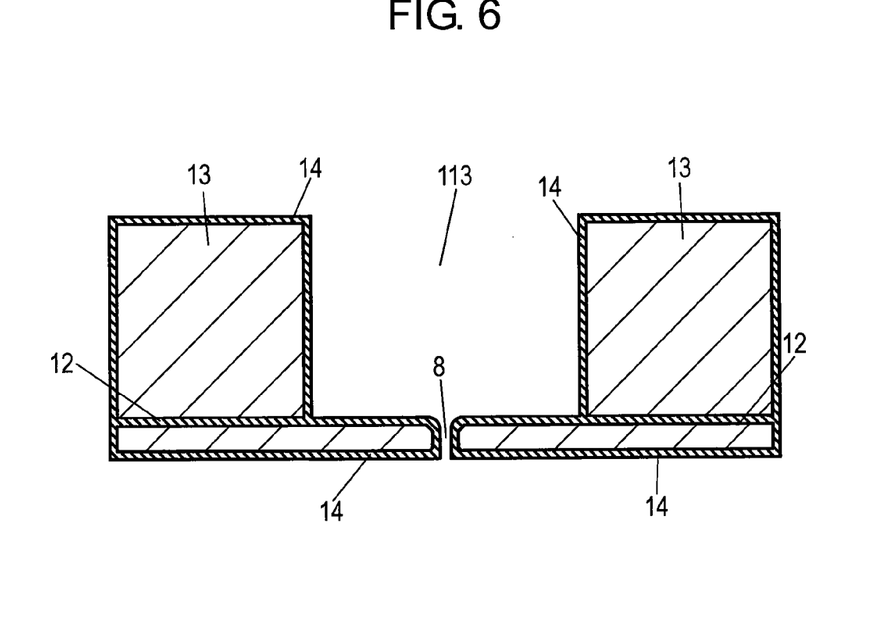
FIG. 6 is a cross-sectional view of the cellular electrophysiology sensor chip for illustrating the method of manufacturing the sensor chip according to the embodiment.
Figure 7:
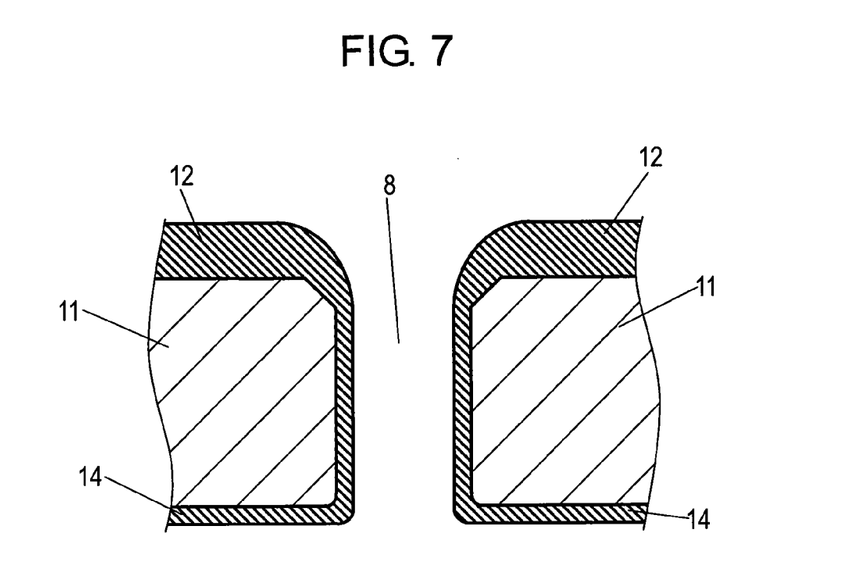
FIG. 7 is an enlarged cross-sectional view of the cellular electrophysiology sensor chip shown in FIG. 6.

Next, when the temperature of the thermal treatment furnace rises to a temperature higher than the melting temperature of silicon dioxide, portion 112 of silicon dioxide layer 12 and the surface of thermally-oxidized film 14 start melting and are smoothed. At this moment, portion 112 of silicon dioxide layer 12 protruding at the opening of through-hole 98 flows so as to sag along the inner wall surface of through-hole 8. Then, through-hole 8 shown in FIGS. 6 and 7 is formed. Through-hole 8 has a curved surface connected continuously to thermally-oxidized film 14 formed on the inner wall surface of through-hole 98 and that is smoothly curved to opening 8A.

The inner wall surface of through-hole 8 includes a smooth curved surface curved toward the inside of through-hole 8 in a direction from the surface of silicon dioxide layer 12 forming diaphragm 2 to the inside of through-hole 8. This structure can consequently provide a flow path that has a cross-sectional area continuously changing from electrode bath 4 to the inside of through-hole 8 and from the inside of through-hole 8 to electrode bath 6, thus reducing a loss due to fluid resistance. As a result, through-hole 8 can accept liquid easily enter into through-hole 8, suck test cell 10A appropriately, and capture the test cell reliably. The smooth surface suppresses air bubbles and can remove the air bubbles efficiently.

Figure 8A:
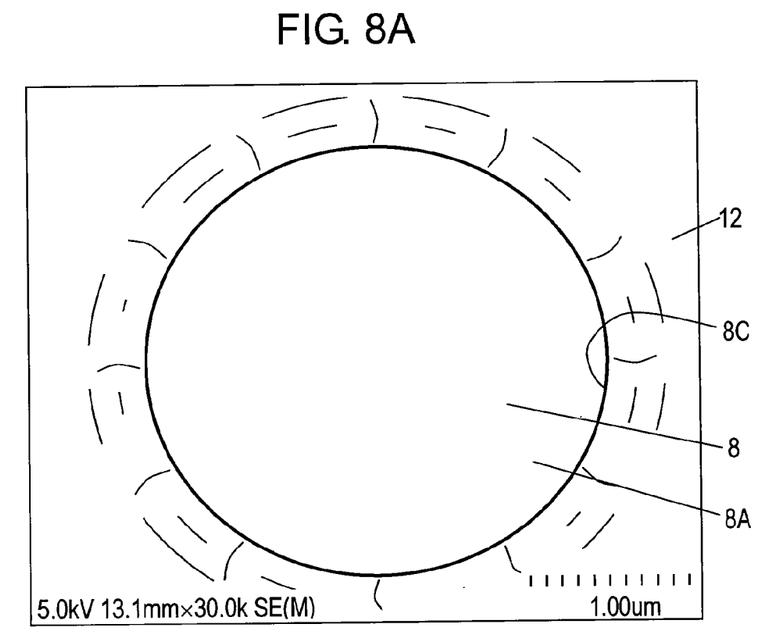
FIG. 8A illustrates a through-hole of the cellular electrophysiology sensor chip according to the embodiment.

FIG. 8A illustrates silicon dioxide layer 12 near opening 8A of through-hole 8. As shown in this figure, silicon dioxide layer 12 has a very smooth surface from opening 8A of through-hole 8 to inner wall surface 8C. The smooth surface preferably allows silicon dioxide layer 12 to be continuously connected to thermally-oxidized film 14 via inner wall surface 8C of through-hole 8. In order to form opening 8A for capturing and retaining test cell 10A, silicon dioxide layer 12 preferably has a thickness not smaller than 0.3 μm. Silicon dioxide layer 12 having a thickness smaller than 0.3 μm makes the surface discontinuous or cannot reproducibly provide the smooth and curved shape.

Figure 8B:
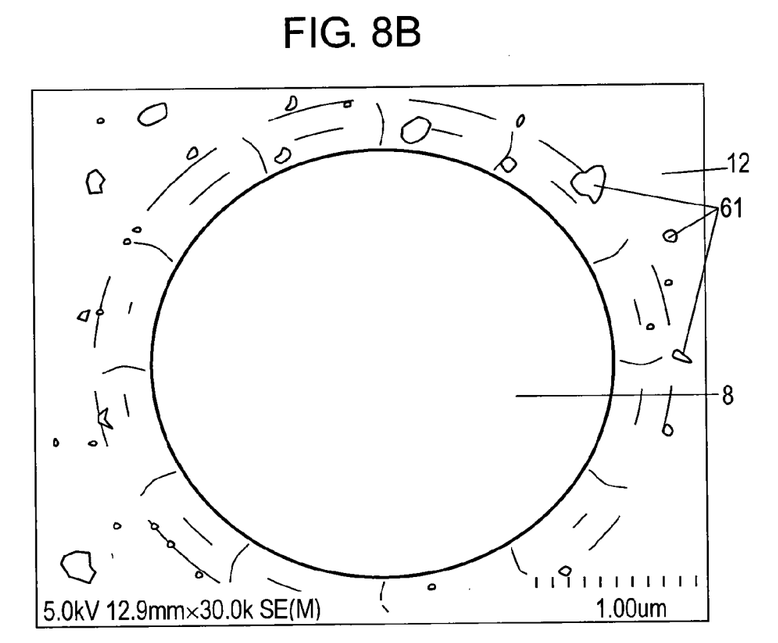
FIG. 8B illustrates a through-hole of the cellular electrophysiology sensor chip according to the embodiment.

FIG. 8B illustrates silicon dioxide layer 12 near opening 8A of through-hole 8 that is subjected to a thermal treatment at a temperature for forming thermally-oxidized film 14. The surface shown in FIG. 8B clearly has an inferior smoothness than the smoothed surface by melting shown in FIG. 8A.

When chip 3 is manufactured by a semiconductor process, silicon particles 61 made of silicon may be attached to silicon dioxide layer 12, as shown in FIG. 8B. Silicon particles 61 prevent a physiochemical change in cell 10A from being measured stably. Even if silicon particles 61 remain near through-hole 8, the silicon particles can be thermally-oxidized by the thermal treatment to change into silicon dioxide and melt. As a result, silicon particles 61 can be unified with silicon dioxide layer 12, thereby providing chip 3 having a surface having superior smoothness and hydrophilicity.

This structure allows test cell 10A to be captured and to stably contact opening 8A of through-hole 8 securely even if cells 10 have different sizes.

When air bubbles are produced in through-hole 8 having a fine size formed in the silicon layer, the air bubbles may cause a fluctuation of the resistance value causing a measurement error. If the air bubbles completely block through-hole 8, electrode baths 4 and 6 are completely insulated from each other, causing the measurement to be substantially impossible. In chip 3 according to this embodiment, the hydrophilic silicon dioxide covers the surface of chip 3 to reduce the air bubbles produced in through-hole 8, thus reducing the measurement error of cellular electrophysiology sensor 1.

Raised portion 18A has a smooth surface having square mean roughness Rq at opening 8A of through-hole 8 not larger than 5.0 nm and a smooth surface having square mean roughness Rq at an upper surface of diaphragm 2 not smaller than 5.0 nm. As shown in FIG. 3A, test cell 10A can be captured along the curved surface of opening 8A, and chip 3 can cause test cell 10A to securely contact opening 8A of through-hole 8, thus improving the measurement accuracy of cellular electrophysiology sensor 1.

The shape of through-hole 8 and the shape of opening 8A of through-hole 8 can be easily changed by the temperature and time at which changing silicon dioxide layer 12 and thermally-oxidized film 14 are heated to melt.

As shown in FIG. 3B, the period of time of the melting is adjusted to easily adjust the position having minimum inner diameter Rmin in through-hole 8. Since minimum inner diameter Rmin is sufficiently smaller than the diameter of cell 10A, test cell 10A is securely retained without passing through through-hole 8. Thus, the shape of opening 8A of through-hole 8 and the shape of through-hole 8 can be easily adjusted so as to be suitable for the size of test cell 10A.

Figure 9:
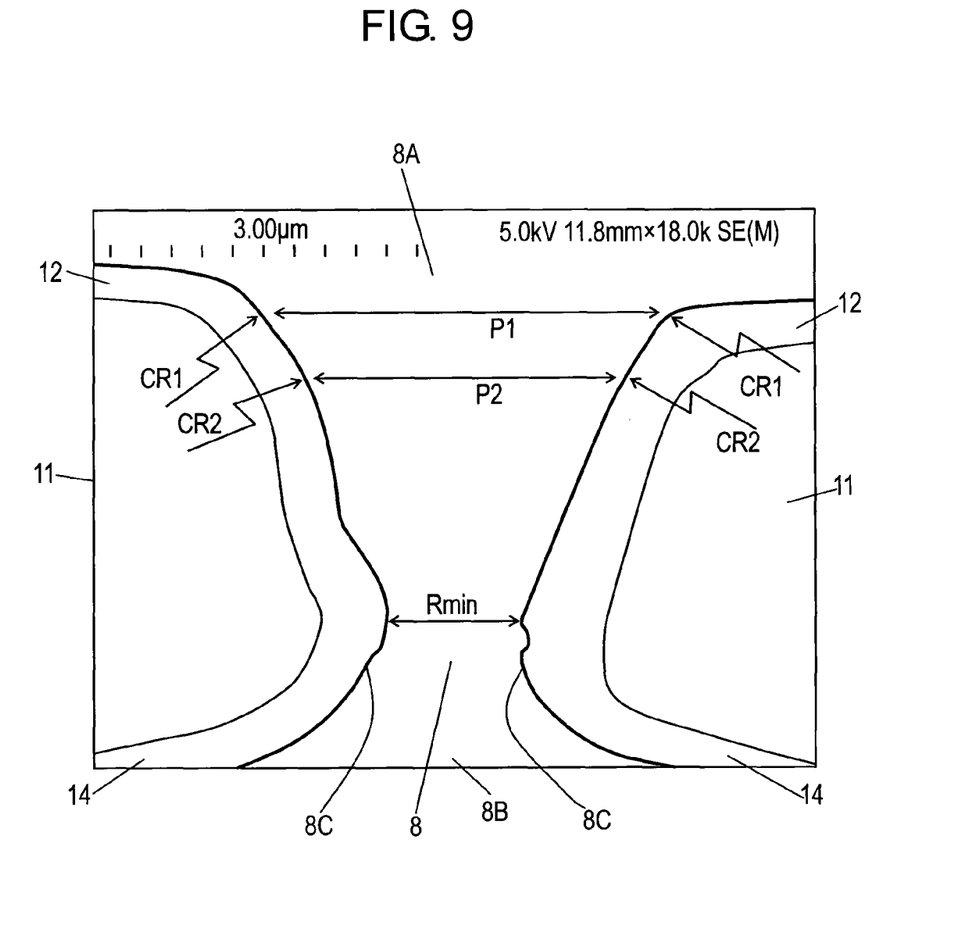
FIG. 9 illustrates a cross section of another cellular electrophysiology sensor chip according to the embodiment.

FIG. 9 is a cross-sectional view of another chip 3 according to the embodiment. If the silicon dioxide layer 12 of chip 3 shown in FIG. 3B is heated to melt for the time shorter than the time to heat and melt silicon dioxide layer 12 at a temperature of 1150° C., the position having minimum inner diameter Rmin becomes closer to opening 8B than opening 8A as shown in FIG. 9. Furthermore, curvature radius CR2 of inner wall surface 8C at position P2 on through-hole 8 is different from curvature radius CR1 of inner wall surface 8C at position P1 different from position P2. Specifically, position P1 is closer to opening 8A than position P2 is, and curvature radius CR1 is smaller than curvature radius CR2. This shape can more securely retain test cell 10A.

As described above, the heating and melting temperature and time can be appropriately adjusted to adjust the shape of through-hole 8 appropriately to the size, shape, and property of cell 10.

According to the embodiment, terms indicating a direction, such as "upper surface" and "lower surface" indicates a relative direction that depends only on the relative positional relation among components, such as silicon layers 11 and 13 and silicon dioxide layer 12, of the cellular electrophysiology sensor, and do not indicate any absolute direction, such as a vertical direction.

INDUSTRIAL APPLICABILITY

A cellular electrophysiology sensor chip according to the present invention captures test cells stably and provides a gigaseal even if test cells have different properties. The cellular electrophysiology sensor chip is applicable to metical and biotechnology fields requiring accurate and efficient measurement.

REFERENCE NUMERALS

1 Cellular Electrophysiology Sensor
2 Diaphragm
3 Chip
4 Electrode Bath (First Electrode Bath)
5 Electrode (First Electrode)
6 Electrode Bath (Second Electrode Bath)

7 Electrode (Second Electrode)
8 Through-Hole
8A Opening
8C Inner Wall Surface
10A Test Cell
11 Silicon Layer
12 Silicon Dioxide Layer
13 Supporter
14 Thermally-Oxidized Film

The invention claimed is:

1. A method of manufacturing a chip for a cellular electrophysiology sensor, comprising:
providing a wafer having a silicon layer and a silicon dioxide layer provided on an upper surface of the silicon layer;
forming a through-hole passing through the silicon layer and the silicon dioxide layer of the wafer, the through-hole having an opening which opens at the silicon dioxide layer;
forming a thermally-oxidized film mainly containing silicon dioxide on a portion of the silicon layer located on an inner wall surface of the through-opening; and
melting the thermally-oxidized film and the silicon dioxide layer to unify the thermally-oxidized film with the silicon dioxide layer at the opening.

2. The method according to claim 1, further comprising
forming a recess extending from the inner wall surface of the through-hole along a lower surface of the silicon dioxide layer such that a portion of the silicon dioxide layer protrudes from the recess, wherein
said melting the thermally-oxidized film and the silicon dioxide layer to unify the thermally-oxidized film with the silicon dioxide layer comprises melting the protruding portion of the silicon dioxide layer and the thermally-oxidized film to unify the protruding portion of the silicon dioxide layer with the thermally-oxidized film at the opening.

3. The method according to claim 2,
wherein the recess has a wall surface connected to the lower surface of the silicon dioxide layer,
wherein said method further comprises causing the portion of the silicon dioxide layer which protrudes from the recess to sag on the wall surface of the recess, and
wherein said melting the thermally-oxidized film and the silicon dioxide layer to unify the thermally-oxidized film with the silicon dioxide layer comprises melting the sagging portion of the silicon dioxide layer and the thermally-oxidized film to unify the protruding portion of the silicon dioxide layer with the thermally-oxidized film at the opening.

4. The method according to claim 3, wherein the wall surface of the recess flares towards the lower surface of the silicon dioxide layer.

* * * * *